US012778639B2

(12) United States Patent
Biedermann et al.

(10) Patent No.: US 12,778,639 B2
(45) Date of Patent: Nov. 3, 2026

(54) COUPLING ASSEMBLY FOR COUPLING A ROD TO A BONE ANCHORING ELEMENT, POLYAXIAL BONE ANCHORING DEVICE AND MODULAR STABILIZATION DEVICE

(71) Applicant: BIEDERMANN TECHNOLOGIES GMBH & CO. KG, Donaueschingen (DE)

(72) Inventors: Lutz Biedermann, VS-Villingen (DE); Wilfried Matthis, Weisweil (DE); Dimosthenis Dandanopoulos, VS-Schwenningen (DE); Achim Schünemann, VS-Mühlhausen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 0 days.

(21) Appl. No.: 19/309,053

(22) Filed: Aug. 25, 2025

(65) Prior Publication Data

US 2025/0375221 A1 Dec. 11, 2025

Related U.S. Application Data

(63) Continuation of application No. 18/654,637, filed on May 3, 2024, now Pat. No. 12,402,918, which is a (Continued)

(30) Foreign Application Priority Data

Sep. 19, 2013 (EP) .................................... 13185176

(51) Int. Cl.
*A61B 17/70* (2006.01)

(52) U.S. Cl.
CPC ...... *A61B 17/7032* (2013.01); *A61B 17/7002* (2013.01); *A61B 17/7035* (2013.01); *A61B 17/7037* (2013.01)

(58) Field of Classification Search
CPC ............................................ A61B 17/70–7046
See application file for complete search history.

(56) References Cited

U.S. PATENT DOCUMENTS 8,100,946 B2 1/2012 Strausbaugh et al.
9,333,016 B2 5/2016 Biedermann et al.
(Continued)

FOREIGN PATENT DOCUMENTS

EP 1 935 358 A1 6/2008
EP 2 070 485 A1 6/2009
(Continued)

OTHER PUBLICATIONS

Extended European Search Report for European Application No. 13185176.8, European Search Report dated Feb. 5, 2014 and mailed Feb. 12, 2014 (7 pgs.).

*Primary Examiner* — Eduardo C Robert
*Assistant Examiner* — Steven J Cotroneo
(74) *Attorney, Agent, or Firm* — Womble Bond Dickinson (US) LLP

(57) ABSTRACT

A coupling assembly is provided comprising a receiving part (6) having a first end (6*a*), a second end (6*b*) and a central axis (C) extending through the first end and second end,
a recess (62) for receiving a rod (100,101), and
an accommodation space (61*a*,61*b*) for accommodating a head (3) of an anchoring element (1), the accommodation space having an opening (72) at the second end (6*b*) for inserting the head (3),
a pressure element (7,7') configured to be positioned at least partly in the accommodation space, the pressure element having a first end (7*a*) and a second end (7*b*), wherein the second end (7*b*) is configured to be positioned closer towards the second end (6*b*) of the receiving part than the first end (7*a*), and a flexible portion (74,75,76,77) to clamp an inserted head (3);
(Continued)

wherein the flexible portion (74,75,76,77) comprises a hollow interior chamber (71) for accommodating a head of a bone anchoring element therein;

a rod receiving element (8,8') that is a separate part comprising a groove (81) for supporting an inserted rod (100, 101);

characterized in that the pressure element (7,7') further comprises at least one spring portion (79*a*,79*b*), the spring portion extending over a length in circumferential direction around the central axis (C) and being compressible in a radial direction; wherein the spring portion (79*a*, 79*b*) is configured to engage an engagement structure (65,66,67) at an inner wall of the receiving part (6) to be prevent movement of the pressure element towards the first end of the receiving part.

24 Claims, 12 Drawing Sheets

Related U.S. Application Data continuation of application No. 17/324,524, filed on May 19, 2021, now Pat. No. 12,011,192, which is a continuation of application No. 15/918,762, filed on Mar. 12, 2018, now Pat. No. 11,039,860, which is a continuation of application No. 14/490,569, filed on Sep. 18, 2014, now Pat. No. 9,943,338.

(60) Provisional application No. 61/879,916, filed on Sep. 19, 2013.

(56) References Cited

U.S. PATENT DOCUMENTS 9,358,047 B2 * 6/2016 Mishra ............... A61B 17/7037
2004/0225289 A1 11/2004 Biedermann et al.
2005/0216003 A1 9/2005 Biedermann et al.
2007/0055241 A1 * 3/2007 Matthis .............. A61B 17/7032 606/267
2007/0093826 A1 * 4/2007 Hawkes ............. A61B 17/7037 606/279
2007/0093904 A1 4/2007 Biedermann et al.
2007/0118123 A1 * 5/2007 Strausbaugh ...... A61B 17/7032 606/272
2008/0108992 A1 5/2008 Barry et al.
2008/0161931 A1 7/2008 Perez-Cruet et al.
2008/0200956 A1 8/2008 Beckwith et al.
2010/0145394 A1 * 6/2010 Harvey .............. A61B 17/7038 606/305
2010/0152787 A1 * 6/2010 Walsh ................ A61B 17/7037 606/305
2010/0160980 A1 6/2010 Walsh et al.
2010/0234902 A1 9/2010 Biedermann et al.
2011/0009911 A1 1/2011 Hammill, Sr. et al.
2011/0152949 A1 * 6/2011 Biedermann ...... A61B 17/7037 606/305
2012/0059426 A1 * 3/2012 Jackson ................. A61B 17/68 606/305
2012/0277806 A1 * 11/2012 Smith ................ A61B 17/7032 606/308
2013/0013003 A1 * 1/2013 Carbone ............ A61B 17/7032 606/305
2013/0046350 A1 2/2013 Jackson et al.
2013/0096623 A1 4/2013 Biedermann et al.
2014/0142634 A1 * 5/2014 Schlaepfer ........... A61B 17/704 29/428
2014/0228890 A1 8/2014 Raju et al.
2014/0343617 A1 * 11/2014 Hannen .............. A61B 17/8605 606/306
2015/0045835 A1 2/2015 Kim
2015/0119940 A1 4/2015 Jackson et al.

FOREIGN PATENT DOCUMENTS

JP 2008-155028 A 7/2008
JP 2009-142655 A 7/2009
WO WO 2012/064360 A1 5/2012
WO WO 2015/069873 A1 5/2015

* cited by examiner

Fig. 13
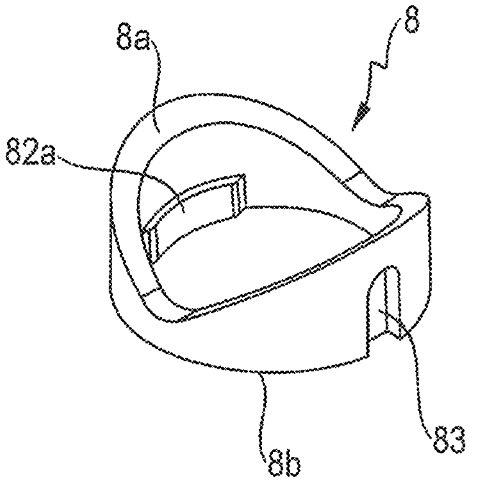
Fig. 14
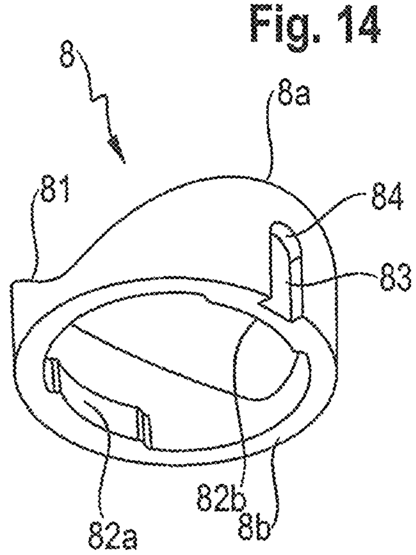
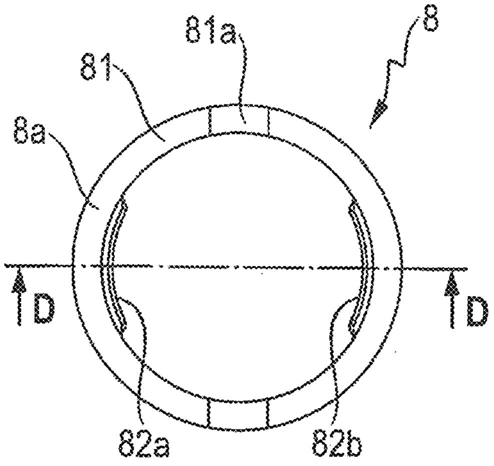
Fig. 15
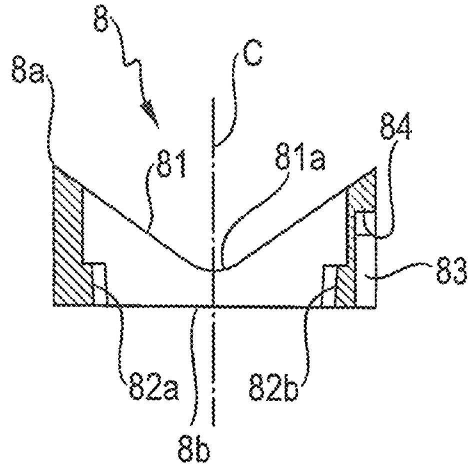
Fig. 16

Fig. 17
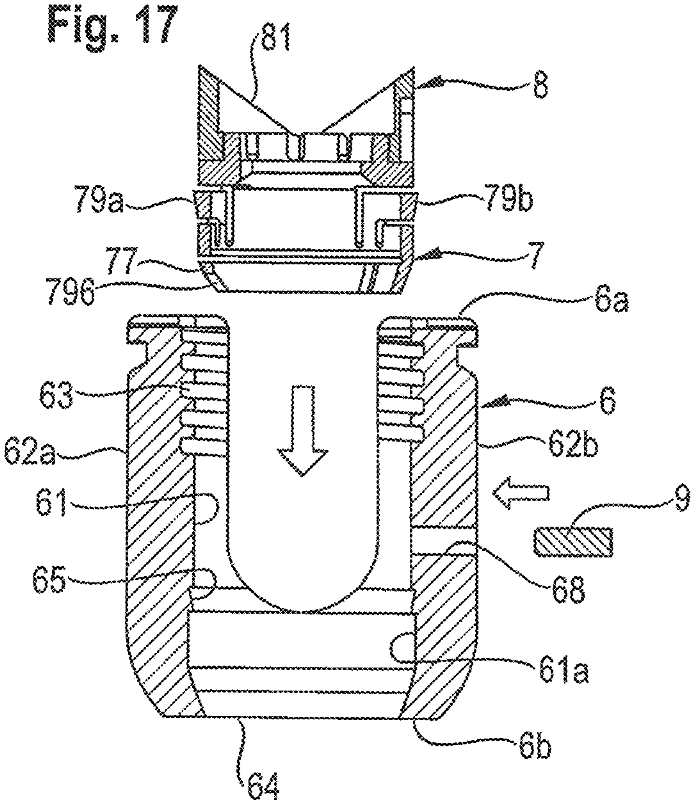
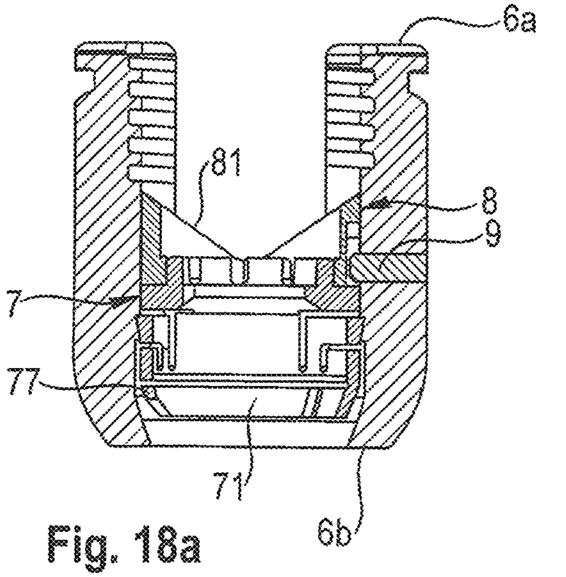
Fig. 18a
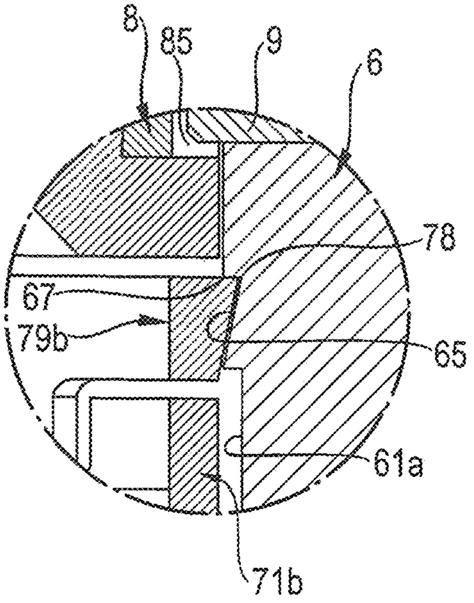
Fig. 18b

Fig. 24
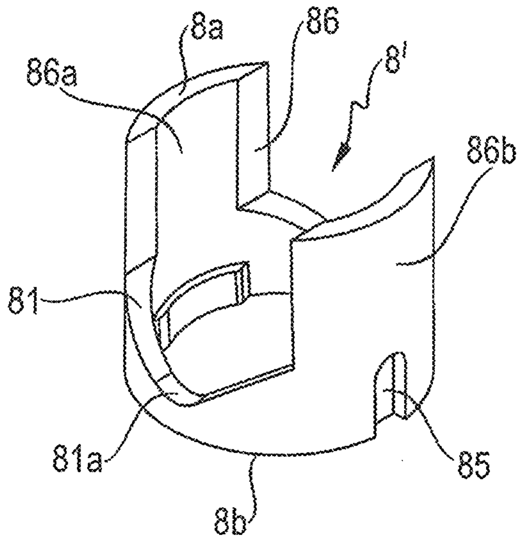
Fig. 25
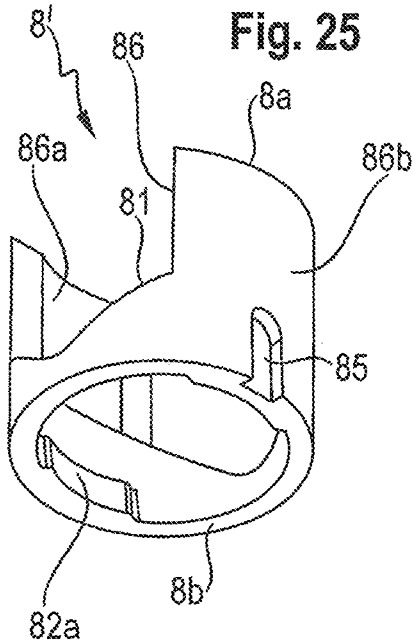
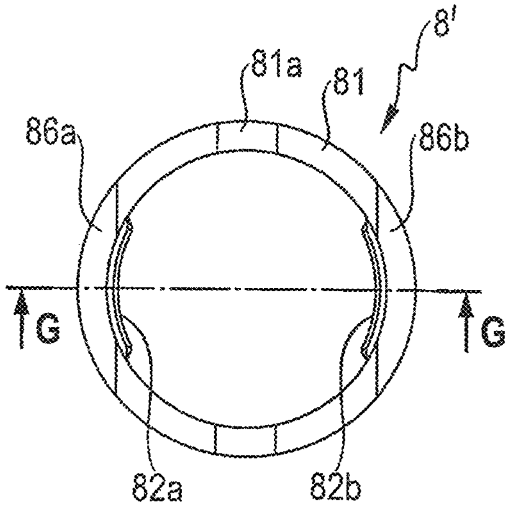
Fig. 26
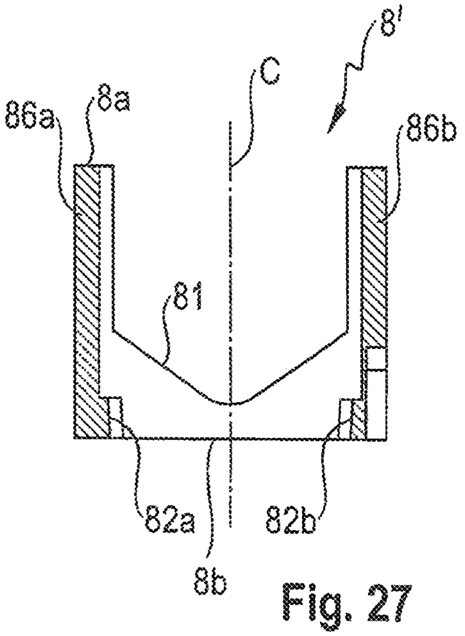
Fig. 27

Fig. 29a
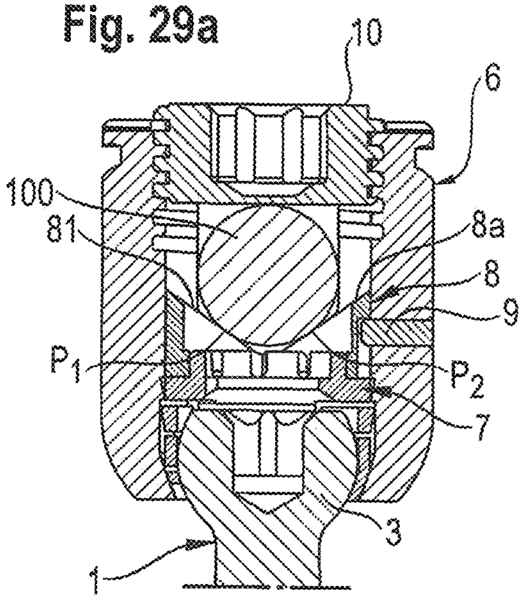
Fig. 29b
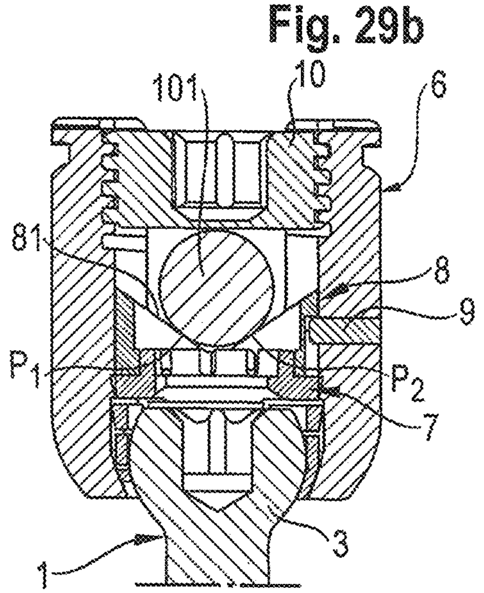
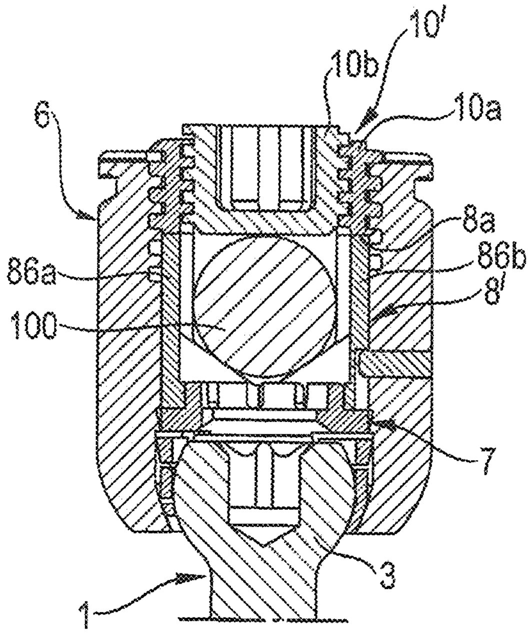
Fig. 30a
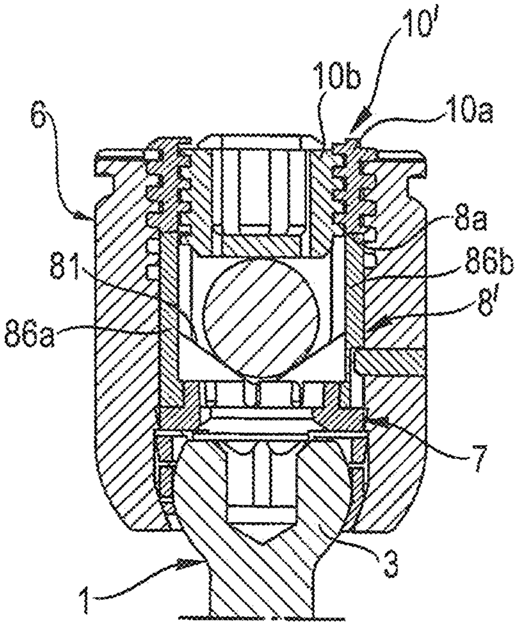
Fig. 30b

COUPLING ASSEMBLY FOR COUPLING A ROD TO A BONE ANCHORING ELEMENT, POLYAXIAL BONE ANCHORING DEVICE AND MODULAR STABILIZATION DEVICE

CROSS-REFERENCE TO RELATED APPLICATION(S)

The present application claims priority to and the benefit of U.S. Provisional Patent Application Ser. No. 61/879,916, filed Sep. 19, 2013, the contents of which are hereby incorporated by reference in their entirety, and claims priority from European Patent Application EP 13 185 176.8, filed Sep. 19, 2013, the contents of which are hereby incorporated by reference in their entirety.

BACKGROUND

Field

The invention relates to a coupling assembly for coupling a rod to a bone anchoring element. The coupling assembly comprises a receiving part with a recess for receiving the rod and an accommodation space for accommodating a head of the bone anchoring element, a pressure element to clamp the head and a separate rod receiving element that is connectable to the pressure element and configured to support the rod. The pressure element comprises at least one spring portion that is extending over a length in a circumferential direction and that is configured to engage a portion of an inner wall of the receiving part so that the pressure element is held in a position that prevents an inserted bone anchoring element from being removed. The invention further relates to a bottom loading type polyaxial bone anchoring device with such a coupling assembly. Still further, the invention relates to a modular polyaxial bone anchoring device comprising the coupling assembly with at least two different rod receiving elements that can be used interchangeably with at least two associated closure mechanisms. Finally the invention relates to a modular stabilization device using the polyaxial bone anchoring device and at least two stabilizations rods having a different diameter or one rod with at least two sections having a different diameter.

DESCRIPTION OF RELATED ART

US 2010/0234902 A1 describes a receiving part for receiving a rod for coupling the rod to a bone anchoring element, the receiving part including a receiving part body with a channel for receiving the rod and defining an accommodation space for accommodating a head of a bone anchoring element and a pressure element at least partially provided in the accommodation space. In one embodiment the pressure element comprises two upstanding resilient fingers with outwardly directed portions at their free ends that can snap below pins extending through the wall of the receiving part in order to secure a pre-locking position of the pressure element in which the head can no longer be removed through the bottom end of the receiving part.

US 2010/0160980 A1 describes a locking mechanism and a method of fixation of a bone screw and a rod to the spine. The locking mechanism includes a body, an insert, a rod seat and a set screw. The body includes a bottom portion configured to receive the bone screw and the insert, but prevents the insert and the bone screw from passing therethrough once the insert and the bone screw are engaged. The rod seat is between the rod and the insert.

SUMMARY

It is an object of the invention to provide an improved coupling assembly for a bottom loading type polyaxial bone anchoring device and such a polyaxial bone anchoring device that allows an improved or easier handling during surgery. Furthermore, it is an object to provide a modular polyaxial bone anchoring device and a modular stabilization device that offers a greater variety of applications based on the modularity of the system.

The object is solved by a coupling assembly according to claim 1, a polyaxial bone anchoring device according to claim 15, a modular polyaxial bone anchoring device according to claim 16 and a modular stabilization device according to claim 17.

Further developments are given in the dependent claims.

The coupling assembly comprises a pressure element that has at least one spring portion extending over a length in a circumferential direction and that is compressible in a radial direction. The spring portion is configured to engage an engagement structure of the inner wall of the receiving part. In a first engagement position, the spring portion engages a first engagement structure of the inner wall of the receiving part to prevent upward movement of the pressure element in the receiving part during insertion of the head of the bone anchoring element. In a second engagement position, the spring portion engages a second engagement structure of the inner wall of the receiving part in a pre-locking position, wherein the bone anchoring element is prevented from being pulled out from the lower opening of the receiving part.

In the pre-locking position of the pressure element, the head of the bone anchoring element may be held by a frictional force exerted by the pressure element onto the head. The frictional force may be such that pivoting of the head is still possible by applying a force to overcome the frictional force.

According to an embodiment of the invention, the flexible portion of the pressure element has a circumferentially extending slit forming a slit ring or a portion of a slit ring at the bottom end of the pressure element. The slit ring can expand in a radial direction to allow for insertion of the head of the bone anchoring element. A force necessary for inserting the head into such a flexible portion of the pressure element is reduced compared to pressure elements that have a flexible portion with only longitudinal or coaxial slits. Therefore, the assembly of the polyaxial bone anchoring device is facilitated.

The coupling assembly can be assembled in situ with a bone anchoring element that has been already inserted into a bone or a vertebra.

In an embodiment, the pressure element may have a recessed portion at its lower end that allows the shank of the bone anchoring element to pivot at a larger angle to one side compared to the opposite side. The pressure element further may have an indication feature configured to cooperate with an instrument to indicate the position of the recessed portion that provides the greater pivot angle. The enlarged pivot angle in one direction may be needed for special applications, for example applications in the cervical spine.

The rod receiving element may have a groove with a shape that allows to support rods or rod sections having a different diameter. Therefore, a modular stabilization device is provided that includes the bone anchoring device and a variety of rods with different diameter or one or more rods that have a change in the diameter over the length of the rod. This renders the polyaxial bone anchoring device suitable for many different applications that depend on the diameter of the rods to be used.

In an embodiment, a first type of a rod receiving element has a first height in the axial direction that is smaller than the diameter of a rod to be supported. The first type of rod receiving element is configured to be used with a single part locking device that locks the head and the rod simultaneously.

In another embodiment the rod receiving element has a second height in the axial direction that is greater than the largest diameter of a rod to be supported. The second type of rod receiving element is configured to be used with a two part locking device that locks the head and the rod independently.

A modular polyaxial bone anchoring device includes a bone anchoring element, the coupling assembly with the first type of rod receiving element and a single part locking device and the second type of rod receiving element with a two part locking device. The first type of rod receiving element with the single part locking device and the second rod receiving element with the two part locking device can be used interchangeably. The assembly of the polyaxial bone anchoring device is easy. Therefore, a kit comprising the modular parts can be provided and the assembly can be made on demand.

The modular polyaxial bone anchoring device furthermore can include several bone anchoring elements that may differ in regard of their length of the shank, their anchoring features of the shank, such as different thread types, thread pitches, different diameter of the shank, and in regard of cannulated on non-cannulated shanks.

The modularity in terms of the bone anchoring element and the type of closure element to be used as well as the modularity in terms of the rods that can be employed opens for the surgeon the choice between a large variety of implants. In addition, the costs for stop-keeping may be reduced.

BRIEF DESCRIPTION OF THE DRAWINGS

Further features and advantages of the invention will become more apparent from the description of various embodiments using the accompanying drawings. In the drawings:

FIG. 13 shows a perspective view from above of a rod receiving element according to a first embodiment;

FIG. 14 shows a perspective view from the bottom of the rod receiving element of FIG. 13;

FIG. 15 shows a top view of the rod receiving element shown in FIGS. 13 and 14;

FIG. 16 shows a cross-sectional view of the rod receiving element of FIGS. 13 and 14 along line D-D in FIG. 15;

FIG. 17 shows a cross-sectional view of a first step of assembling the coupling assembly according to the first embodiment;

FIG. 18*a* shows a cross-sectional view of a second step of assembling the coupling assembly according to the first embodiment;

FIG. 18*b* shows an enlarged cross-sectional view of a detail of FIG. 18*a;*

FIG. 24 shows a perspective view from above of a rod receiving element of a coupling assembly according to a second embodiment;

FIG. 25 shows a perspective view from the bottom of the rod receiving element shown in FIG. 24;

FIG. 26 shows a top view of the rod receiving element shown in FIGS. 24 and 25;

FIG. 27 shows a cross-sectional view of the rod receiving element shown in FIGS. 24 and 25 a long line G-G in FIG. 26;

FIG. 29*a* shows a cross-sectional view of the polyaxial bone anchoring device according to the first embodiment with an inserted rod having a first diameter and a single part locking device;

FIG. 29*b* shows a cross-sectional view of the polyaxial bone anchoring device according to the first embodiment with an inserted rod having a second diameter and a single part locking device;

FIG. 30*a* shows a cross-sectional view of a polyaxial bone anchoring device according to the second embodiment with an inserted rod having a first diameter and a two part locking device; and FIG. 30*b* shows a cross-sectional view of the polyaxial bone anchoring device according to the second embodiment with an inserted rod having a second diameter and a two part locking device.

DETAILED DESCRIPTION

Figure 1:
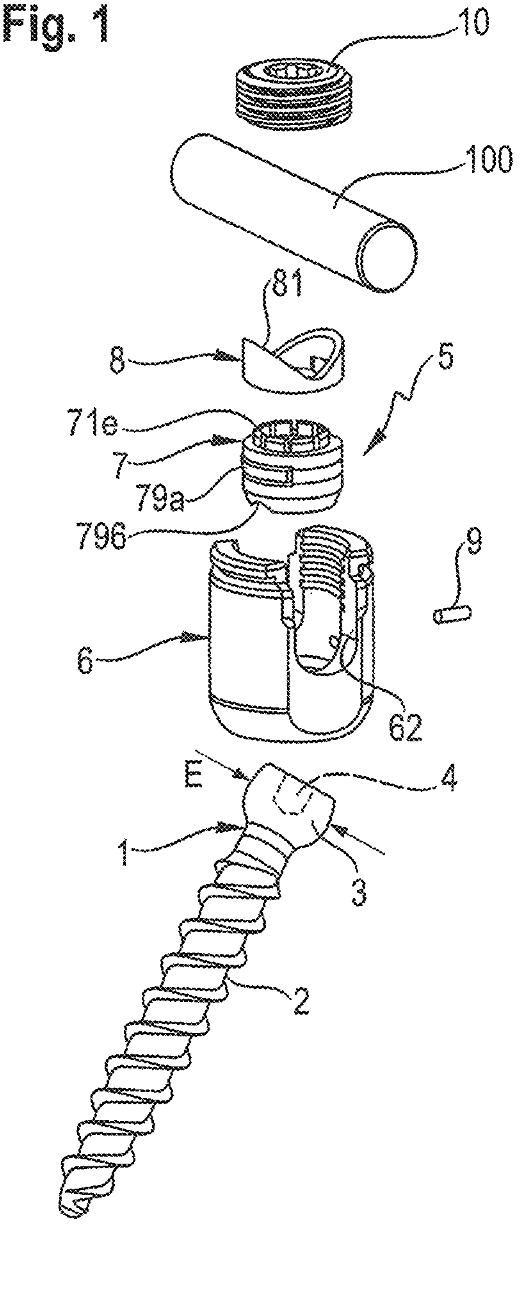
FIG. 1 shows a perspective exploded view of a first embodiment of a bone anchoring device.
Figure 2:
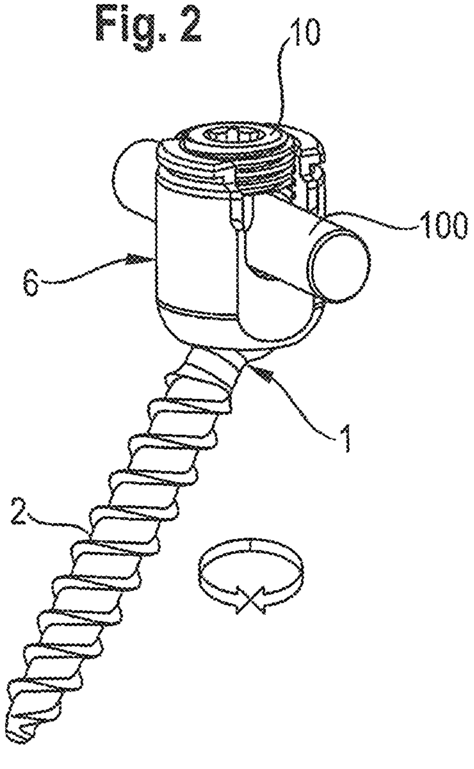
FIG. 2 shows a perspective view of the bone anchoring device of FIG. 1 in an assembled state.

Referring to FIGS. 1 and 2, a bone anchoring device according to a first embodiment includes a bone anchoring element 1 in the form of a bone screw having a shank 2 that is at least partially provided with a bone thread and a head 3. The head 3 has a spherical segment-shaped surface portion including a greatest outer diameter E of the sphere and a flat free end with a recess 4 for engagement with a screwing-in tool.

The bone anchoring device further includes a coupling assembly 5 for receiving a stabilization rod 100 and for coupling the stabilization rod 100 to the bone anchoring element 1. The coupling assembly 5 includes a receiving part 6 for receiving the head of the bone anchoring element 1 and for receiving the rod 100 and a pressure element 7 configured to be arranged in the receiving part 6. The pressure element 7 serves for locking the head 3 in the receiving part 6. The coupling assembly further comprises a rod receiving element 8 that is connectable to the pressure element 7 and that serves for providing support for an inserted rod. A pin 9 may be employed for securing a rotational position of the rod receiving element 8 so that a support surface for the rod is aligned with a recess of the receiving part 6 through which the rod extends as described below.

Further, a locking element 10 in the form of an inner screw is provided for securing the rod 100 in the receiving part 6 and for exerting a force via the rod 100 onto the rod receiving element 8 and the pressure element 7 to lock the head 3 in the receiving part 6. The locking element 10 is a single part locking element that is configured to lock the head 3 of the bone anchoring element 1 and the rod 100 simultaneously.

The receiving part 6 will now be explained with reference to FIGS. 1 to 7*b*. The receiving part 6 has a first end 6*a* that is a top end and an opposite second end 6*b* that forms a bottom end, a central axis of symmetry C passing through the first end 6*a* and the second end 6*b*. A bore 61 is provided that is coaxial to the central axis C. In a first region adjacent to the first end 6*a* the receiving part 6 has a substantially U-shaped recess 62 with a bottom directed towards the second end 6*b* and two free lateral legs 62*a*, 62*b* extending towards the first end 6*a*. On the legs 62*a*, 62*b*, and internal thread 63 is provided that cooperates with the locking element 10. The channel formed by the U-shaped recess 62 is sized so as to receive the rod 100 therein for connecting at least two or a plurality of bone anchoring devices. In the region of the legs 62*a*, 62*b* up to substantially a height in axial direction that is defined by the bottom of the U-shaped recess 62, the bore 61 has a first diameter. In a region below the legs 62*a*, 62*b*, the bore 61 has a widened portion 61*a* with a diameter greater than the first inner diameter of the first portion. Between the second end 6*b* and the widened portion 61*a*, the bore 61 has a narrowing portion 61*b* that tapers towards the second end 6*b* with a cone angle. An opening 64 is provided at the second end 6*b*, the diameter of the opening 64 being larger than the largest diameter E of the head 3 to allow the insertion of the head 3 from the second end 6*b* of the receiving part 6. The widened portion 61*a* and the narrowing portion 61*b* define an accommodation space for the head 3 of the bone anchoring element 1.

Between the first portion of the bore 61 that is located adjacent to the first end 6*a* and the widened portion 61*a* of the bore 61, there is a recess 65 that extends circumferentially in the inner wall of the receiving part and that has a substantially conical shape widening in a direction from the second end 6*b* towards the first end 6*a*. As can be seen in detail in FIG. 7*b*, the size of the recess 65 is such that at its end facing the second end 6*b* of the receiving part it has an inner diameter corresponding substantially to the inner diameter of the first portion of the bore 61 and therefore forms an annular inwardly protruding edge 66 on the upper end of the widened portion 61*a*. The protruding edge 66 defines a first stop. An upper edge of the recess 65 has substantially the same diameter than the first portion of the bore 61 and forms a second edge 67 that defines a second stop. A cone angle of the recess 65 is such that a spring portion provided at the pressure element 7 can be held in the recess 65 in a pre-stressed manner as described below.

At at least one of the legs 62*a*, 62*b*, a transverse bore 68 is provided that extends through the leg, for example through the leg 62*b*, in a direction substantially perpendicular to the central axis C for receiving the pin 9. The pin 9 has such a length, that once it is inserted into the transverse bore 68, it extends a short distance into the bore 61 to provide a stop for securing the rotational position of the rod receiving element 8 as described below. The pin 9 may be flush with the outer surface of the receiving part 6 when inserted.

Referring to FIGS. 8 to 12, the pressure element 7 has a first end 7*a* and a second end 7*b*. The second end 7*b* of the pressure element 7 is configured to be closer to the second end 6*b* of the receiving part 6 than the first end 7*a* of the pressure element 7 when the pressure element 7 is arranged in the receiving part 6. The pressure element 7 is a substantially cap-like part that has a hollow interior chamber 71 with an opening 72 at the second end 7*b*, wherein the hollow interior chamber 71 is configured and sized so as to accommodate and hold the head 3 of the bone anchoring element therein. An opening 73 near the first end 7*a* that is in connection with the hollow interior chamber 71 allows to access the recess 4 of the head 3 with a tool from the first end 7*a* of the pressure element 7. The lower opening 72 has a size so as to allow the insertion of the head 3 from the second end 7*b*. A lower portion 71*a* of the pressure element 7 adjacent to the second end 7*b* narrows towards the second end 7*b* with a an outer surface matching the shape of the narrowing portion 61*b* of the receiving part. In the embodiment shown, the outer surface of the lower portion 71*a* tapers in a direction towards the second end 7*b*, wherein the taper corresponds substantially to the taper of the narrowing portion 61*b* of the receiving part 6.

At a distance from the second end 7*b*, a circumferentially extending slit 74 is provided. The slit 74 extends around the central axis C of the pressure element 7 along a plane substantially perpendicular to the central axis C when the pressure element 7 is arranged in the receiving part 6. Further, the slit 74 extends around more than 180°, preferably more than 270° and further preferably more than 340° around the central axis C. By means of the slit 74, a ring-shaped portion at the second end 7*b* is provided that is integrally connected to the rest of the pressure element 7 by a wall portion forming a connecting strip 75. The connecting strip 75 has such a length in the circumferential direction that it provides a stable connection of the ring-shaped portion to the rest of the pressure element 7. At one end of the circumferentially extending slit 74, there is a substantially vertical slit 76 that extends from the second end 7*b* fully through the ring-shaped portion into the circumferentially extending slit 74. By means of this, the ring-shaped portion is cut through or split in a circumferential direction and forms a slit ring 77 that can be expanded and compressed in a radial direction. The outer surface of the slit ring 77 forms the narrowing outer surface of the lower portion

71*a* that narrows towards the second end of the pressure element 7. A position and size of the slit ring 77 is such that when the head 3 of the bone anchoring element 1 is inserted through the opening 72 into the hollow interior chamber 71, the slit ring 77 expands so that the width of the vertical slit 76 becomes larger, and when the head 3 has been fully inserted into the hollow interior chamber 71, the slit ring 77 encompasses the head 3 at or below a position of the largest diameter E of the head 3 in a direction towards the shank 2. An inner surface of the pressure element 7 in the region of the slit ring 77 is spherical segment-shaped with a size that is adapted to the size of the head 3.

A following portion 71*b* of the pressure element 7 adjacent to the slit ring 77 is substantially cylindrical with an outer diameter that is smaller than an inner diameter of the widened portion 61*a* of the receiving part 6. A corresponding inner surface is substantially cylindrical with an inner diameter corresponding to or slightly larger than the largest outer diameter E of the head 3.

The pressure element 7 further has an intermediate portion 71*c* that continues from the cylindrical portion 71*b*. The intermediate portion 71*c* has a conical outer surface that widens towards the first end 7*a* of the pressure element 7. An outermost edge 78 of the intermediate portion 71*c* that is facing in the direction of the first end 7*a* protrudes outward. The cone angle of the intermediate portion 71*c* corresponds substantially to the cone angle of the conical recess 65 of the receiving part 6. An inner surface of the intermediate portion 71*c* is cylindrical and has an inner diameter corresponding to the inner diameter of the cylindrical portion 71*b*.

Next, an upper cylindrical portion 71*d* extends from the intermediate portion 71*c* towards the first end 7*a* of the pressure element 7. The upper cylindrical portion 71*d* has an outer diameter that may be substantially the same as the outer diameter of the lower cylindrical portion 71*b* and that is in particular slightly smaller than the inner diameter of the bore 61. The upper cylindrical portion 71*d* comprises the coaxial bore 73 and a spherical segment-shaped section 710 that is part of the hollow interior chamber 71 and has a radius adapted to the spherical segment-shaped head 3 of the bone anchoring element 1. Hence, when the head 3 of the bone anchoring element 1 is inserted into the hollow interior chamber 71 and tilted, as can be seen, for example, in FIG. 3, the spherical segment-shaped section 710 contacts the surface of the head 3.

In the intermediate portion 71*c* two spring portions 79*a*, 79*b* are provided. The spring portions 79*a*, 79*b* are ring segment-shaped and extend around the central axis C around an angle α of approximately 90°, as can be seen in particular in FIG. 11. However, the ring segment-shaped spring portions 79*a*, 79*b* can extend around a smaller or a larger angle around the central axis C, depending on the desired flexibility to be achieved.

Figure 10:
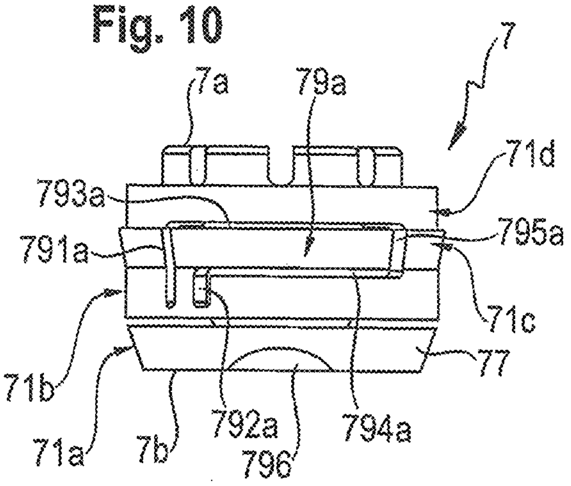
FIG. 10 shows a side view of the pressure element shown in FIGS. 8 and 9.
Figure 11:
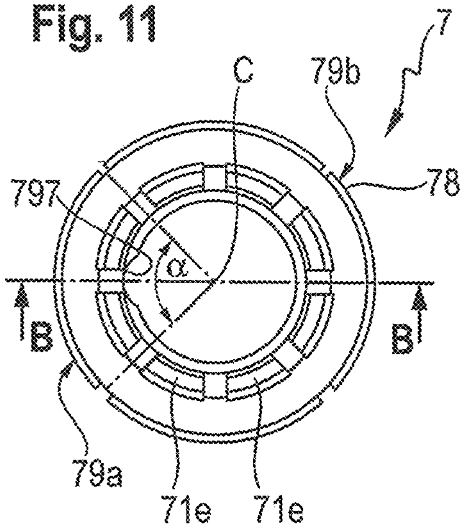
FIG. 11 shows a top view of the pressure element shown in FIGS. 8 and 9.
Figure 12:
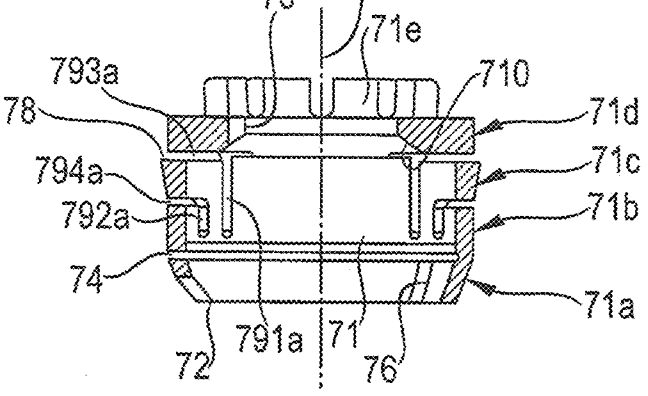
FIG. 12 shows a cross-sectional view of the pressure element of FIGS. 8 and 9 along line B-B in FIG. 11.

The spring portions 79*a*, 79*b* are generated by slits that extend substantially coaxially to the central axis C and slits that extend substantially in a circumferential direction. Referring in particular to FIG. 10, the spring portion 79*a* is formed by the following slits. A first vertical slit 791*a* extends from the lower cylindrical portion 71*b* of the pressure element 7 towards the lower end of the intermediate portion 71*c* in a substantially vertical or coaxial direction with respect to the central axis C. A second vertical slit 792*a* is spaced apart from the first vertical slit 791*a* in a circumferential direction and extends from the lower cylindrical portion 71*b* of the pressure element 7 until the upper end of the intermediate portion 71*c*. A first or upper horizontal slit 793*a* extends from the first vertical slit 791*a* in a circumferential direction around an angle that defines the angle α of the spring portion around the central axis C. A second or lower horizontal slit 794*a* extends from the upper end of the second vertical slit 792*a* in a circumferential direction around an angle slightly less than the angle α around the central axis C. A third vertical slit 795*a* connects the ends of the first horizontal slit 793*a* and the second horizontal slit 794*a*. A width of the vertical slits 791*a*, 792*a*, 795*a* in a circumferential direction may be greater than a width of the horizontal slits 793*a*, 794*a* in an axial direction. Further, the width of the upper horizontal slit 793*a* may be the same as the width of the lower horizontal slit 794*a*.

By the first and second vertical slits 791*a*, 792*a* a strip is formed that connects the ring segment-shaped spring portion 79*a* with the rest of the pressure element 7. By the third vertical slit 795*a*, the ring segment-shaped spring portion 79*a* is provided with a free end in the circumferential direction.

The second ring segment-shaped spring portion 79*b* is formed identically and comprises a first vertical slit 791*b*, a second vertical slit 792*b* and a third vertical slit 795*b* as well as a first upper horizontal slit 793*b* and a second lower horizontal slit 794*b*. The ring segment-shaped spring portions 79*a*, 79*b* are arranged mirror-symmetrical with respect to a mirror plane that contains the central axis C and extends between the first vertical slit 791*a*, 791*b* of each spring portion, as depicted in particular in FIG. 12. Hence, the free ends of the ring segment-shaped spring portions 79*a*, 79*b* point towards each other seen in a circumferential direction.

The spring portions 79*a*, 79*b* are compressible and expandable in a radial direction. When the pressure element 7 is inserted into the bore 61 of the receiving part 6, the spring portions 79*a*, 79*b* are slightly compressed so that the pressure element 7 can move downward in the bore 61. Once the spring portions 79*a*, 79*b* have passed the portion of the bore 61 having the first diameter, they are configured to resiliently snap into the conical recess 65.

The pressure element 7 further comprises adjacent to its first end 7*a* a plurality of upstanding ring segment-shaped projections 71*e* that are spaced apart in a circumferential direction and that are slightly resilient. An outer surface may be slightly tapered so as to provide for a safe connection with the rod receiving element as described below. An inner surface may be cylindrical. The upstanding projections 71*e* are spaced apart from an outer surface of the upper cylindrical portion 71*d* and are surrounding the coaxial bore 73.

Adjacent to the second end 7*b*, there is a recessed portion 796 at the lower edge of the pressure element 7 that is formed by the lower edge of the slit ring 77. The recessed portion 796 has such a shape and size that the shank 2 of the bone anchoring element 1 abuts at a larger pivot angle against the lower edge of the pressure element 7 when it pivots in the direction of the recessed portion 796 as compared to the opposite direction. Therefore, the recessed portion 796 provides for an enlarged pivot angle in only one direction. As can be seen in FIG. 10, the recessed portion 796 may be arranged approximately at the middle of one of the spring portions 79*a*, 79*b*. A second recessed portion 797 is provided at a corresponding circumferential position in the inner wall of the upper cylindrical portion 71*d*. The second recessed portion 797 serves for indicating the position of the first recessed portion 796, for example when the pressure element is engaged with a tool (not shown) that comprises an engagement portion to engage the second recessed portion 797. Such a tool could have a visual indication on its handle, for example, that shows the user the position of the second recessed portion 797 and as a consequence thereof the position of the first recessed portion 796. Hence, the position of the first recessed portion 796 that provides for the enlarged pivot angle can be seen even if the polyaxial bone anchoring device has already been implanted into a bone or a vertebra. The tool can also be used to engage the second recessed portion 797 in a form fit manner and rotate the pressure element to adjust the orientation of the first recessed portion 796.

Figure 3:
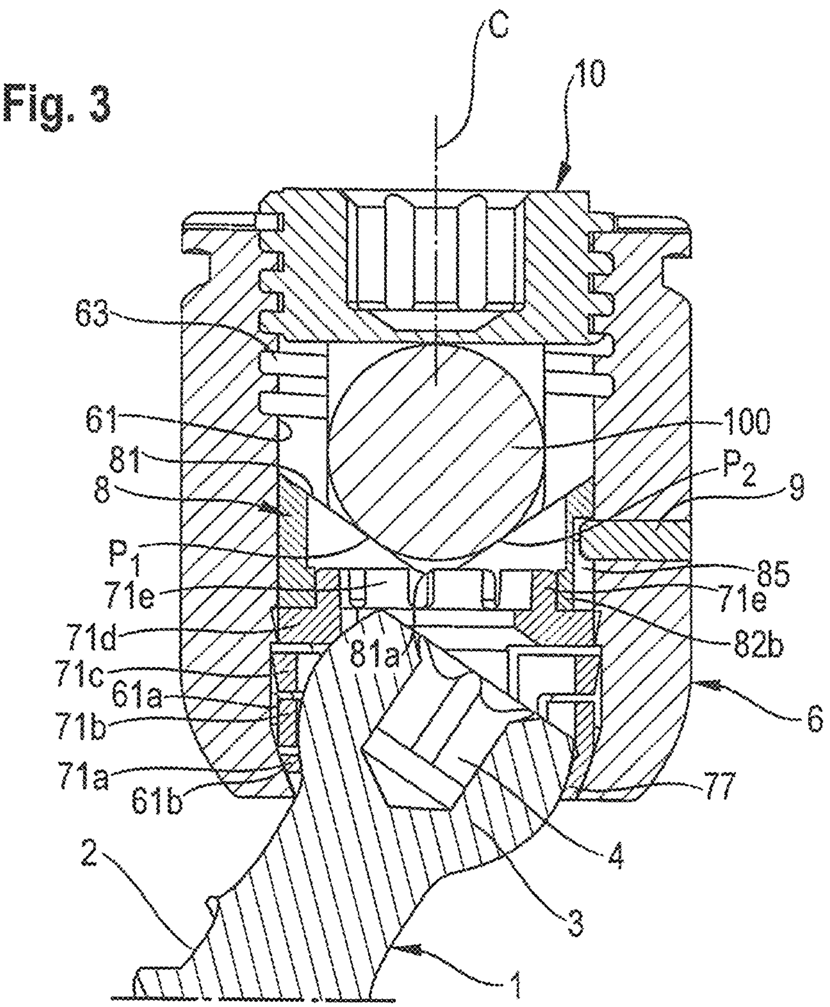
FIG. 3 shows a cross-sectional view of the bone anchoring device according to the first embodiment of FIGS. 1 and 2, the section taken perpendicular to an axis of an inserted rod.
Figure 4:
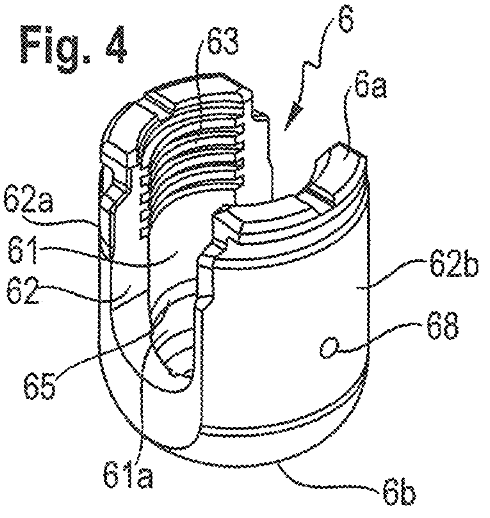
FIG. 4 shows a perspective view from above of a receiving part according to the first embodiment.
Figure 5:
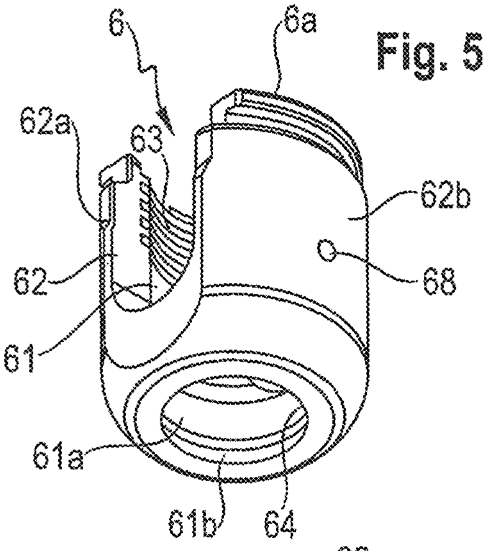
FIG. 5 shows a perspective view from the bottom of the receiving part shown in FIG. 4.
Figure 6:
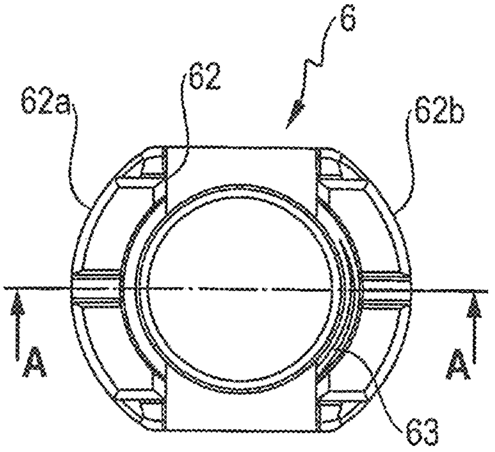
FIG. 6 shows a top view of the receiving part shown in FIGS. 4 and 5.
Figure 7A:
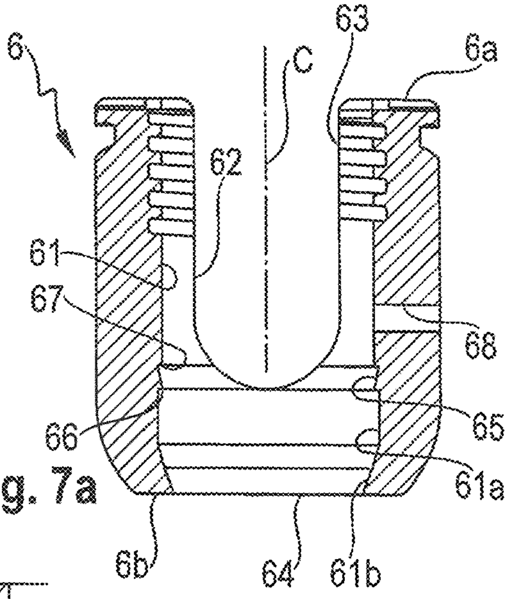
FIG. 7*a* shows a cross-sectional view of the receiving part shown in FIGS. 4 and 5 along line A-A in FIG. 6.
Figure 7B:
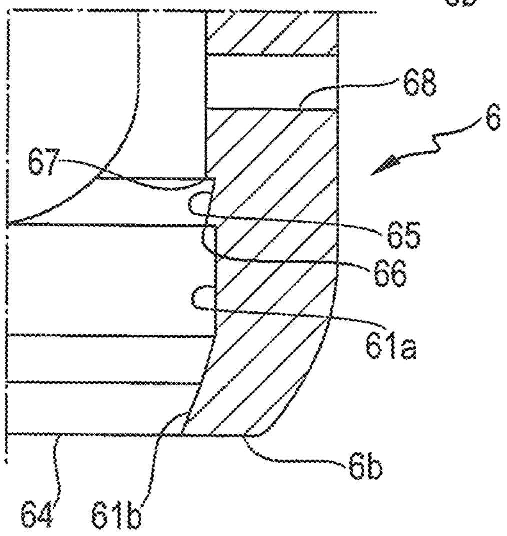
FIG. 7*b* shows an enlarged view of a detail of FIG. 7*a;*
Figure 8:
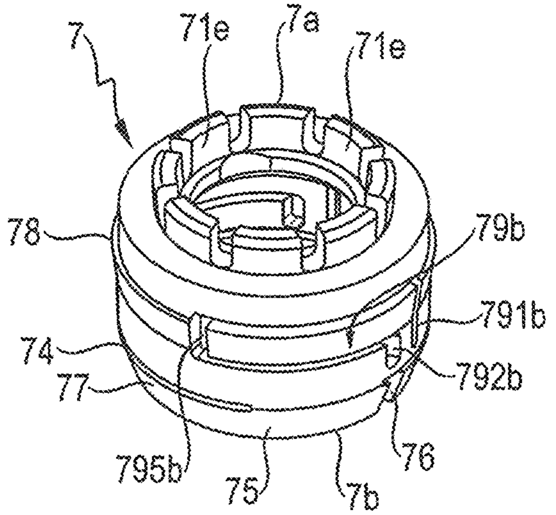
FIG. 8 shows a perspective view from above of a pressure element according to a first embodiment.
Figure 9:
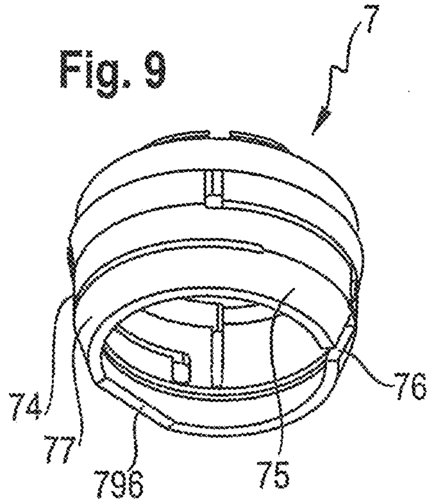
FIG. 9 shows a perspective view from the bottom of the pressure element shown in FIG. 8.

With reference to FIGS. 3 and 13 to 16, the rod receiving element 8 will be described. The rod receiving element 8 is a substantially hollow cylindrical part having a first end 8*a* and an opposite second end 8*b*. A groove 81 having a substantially V-shaped cross section with a rounded bottom 81*a* extends from the first end 8*a* in the direction of the second end 8*b*, as can be seen in particular in FIGS. 13 and 16. The groove 81 defines a longitudinal direction that is parallel to the longitudinal axis of the rod 100 when the rod 100 is inserted. The groove 81 provides a support surface for supporting the rod 100. Referring to FIG. 3, the rod 100 has a circular cross section and is supported in the groove 81 along two contact lines P1, P2 that extend in a direction parallel to the rod axis. Depending on the diameter of the rod section that is supported by the groove 81, the contact lines P1, P2 are located more towards the bottom 81*a* for a rod with a smaller diameter or more towards the first end 8*a* for a rod with a larger diameter than the rod 100 depicted in FIG. 3. Hence, the groove 81 is configured to support different rods having a different diameter or different rod sections of a single rod that have a different diameter.

Adjacent to the second end 8*b*, two opposite annular segment-shaped protrusions 82*a*, 82*b* are provided that extend towards the central axis C in a radial direction and along a certain length in circumferential direction. A height of the annular segment-shaped protrusions 82*a*, 82*b* in the axial direction measured from the second end 8*b* corresponds to a height of the upstanding projections 71*e* of the pressure element. Furthermore, an inner surface of the annular segment-shaped protrusions 82*a*, 82*b* is slightly tapered towards the second end 8*b* and is configured to cooperate with the tapered outer surface of the upstanding projections 71*e* of the pressure element. Once the annular segment-shaped protrusions 82*a*, 82*b* engage the outer wall of the upstanding projections 71*e* of the pressure element, the upstanding projections 71*e* are slightly compressed and abut against the annular segment-shaped protrusions 82*a*, 82*b* so that the pressure element is connected to the rod receiving element 8 and held by a frictional force. The location of the center of the annular segment-shaped protrusions 82*a*, 82*b* in a circumferential direction is at substantially 90° with respect to the bottom 81*a* of the groove 81.

In the outer wall of the rod receiving element on one side of the groove 81, an elongate recess 83 that is substantially coaxial with the central axis C is provided. The elongate recess 83 has a closed end 84 towards the first end 8*a* that serves as an abutment for the pin 9. By the elongate recess 83*a*, a securing element is provided that secures the correct rotational position of the rod receiving element 8. The elongate recess 83 is open towards the second end 8*b*.

A depth of the groove 81 is smaller than a largest diameter of a rod that can be supported by the rod receiving element 8. In other words, the first end 8*a* is located below a top surface of a rod with a largest diameter that can be supported by the rod receiving element 8.

An outer diameter of the rod receiving element 8 is only slightly smaller than an inner diameter of the bore 61 of the receiving part and is preferably flush with an outer diameter of the upper cylindrical portion 71*d* of the pressure element 7 when the pressure element 7 and the rod receiving element 8 are assembled as shown in FIG. 3.

The bone anchoring device as a whole or in parts is made of a bio-compatible material, such as a bio-compatible metal or a metal alloy, for example titanium, stainless steel, a nickel titanium alloy, for example, nitinol, or of bio-compatible plastic materials, such as, for example, polyetheretherketone (PEEK).

Referring to FIG. 17, the coupling assembly 5 is assembled by pre-assembling the pressure element 7 and the rod receiving element 8 such that the upstanding projections 71*e* are inserted and held between the annular segment-shaped protrusions 82*a*, 82*b* of the rod receiving element 8. The orientation of the pressure element 7 relative to the groove 81 of the rod receiving element 8 is such that the center of the spring portions 79*a*, 79*b* are located in circumferential direction at an angle of substantially 90° measured from the longitudinal axis of the groove 81. The pre-assembled pressure element 7 with the rod receiving element 8 is inserted from the first end 6*a* of the receiving part with the second end 7*b* of the pressure element facing in the direction of the second end 6*b* of the receiving part 6. During insertion, the spring portions 79*a*, 79*b* are compressed in a radial direction because the inner diameter of the first portion of the bore 61 in the receiving part 6 has a smaller diameter than the outermost edge 78 of the spring portions 79*a*, 79*b*.

Referring to FIGS. 18*a* and 18*b*, as soon as the pressure element 7 is in a position in which the outermost edge 78 of the spring portions 79*a*, 79*b* has reached the conical recess 65 in the receiving part 6, it snaps behind the protrusion 67 that forms the upper edge of the conical recess 65. Thereby, the spring portions 79*a*, 79*b* are configured to radially expand into the conical recess 65. Thereafter, the pin 9 is inserted into the transverse bore 68 until a front face of the pin 9 extends into the elongate recess 83 provided at the rod receiving element 8. The pin 9 serves for securing the pressure element and the rod receiving element against inadvertent rotation so that the U-shaped recess 62 of the receiving part and the groove 81 of the rod receiving element 8 remain aligned. In this condition, the coupling assembly 5 is pre-assembled and can be used for coupling to a bone anchoring element and to a rod. In the pre-assembled condition it is still possible to rotate the pressure element 7 with respect to the rod receiving element 8 and therefore also with respect to the receiving part 6 so that the orientation of the first recessed portion 796 that defines the direction having the enlarged pivot angle can be adjusted.

Figure 19:
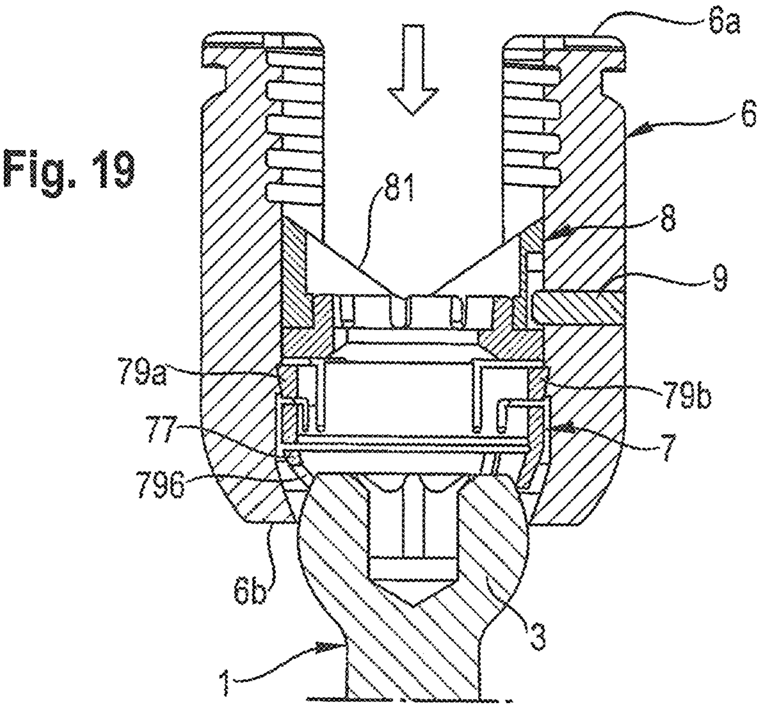
FIG. 19 shows a cross-sectional view of a first step of assembling the polyaxial bone anchoring device according to the first embodiment.
Figure 20:
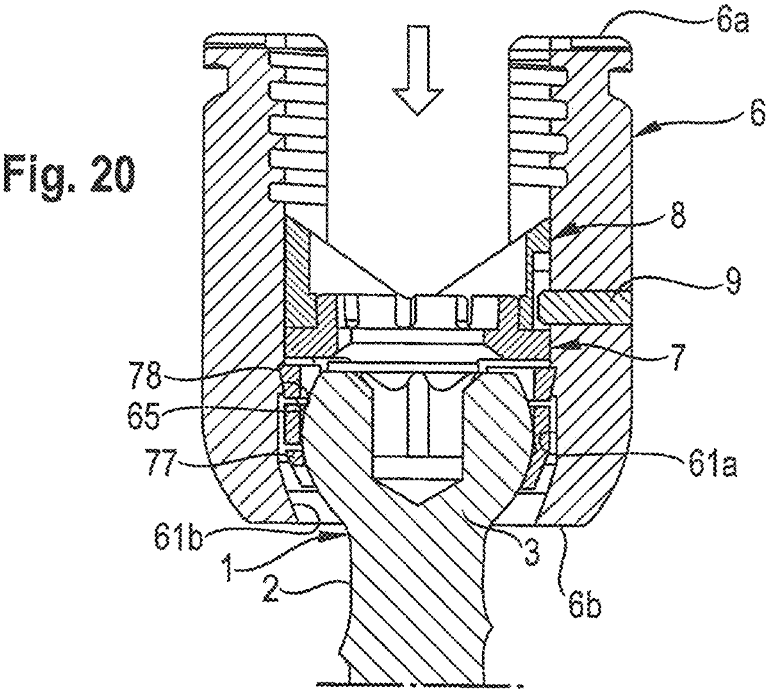
FIG. 20 shows a cross-sectional view of second step of assembling the polyaxial bone anchoring device according to the first embodiment.

Referring further to FIGS. 19 and 20, the use of the coupling assembly 5 together with a bone anchoring element 1 will be explained. As depicted in FIG. 19, first, a suitable bone anchoring element 1 is selected. It may be connected to the coupling assembly first and thereafter inserted into a bone part or a vertebra. Alternatively, the bone anchoring element 1 can be placed first into the implantation sight without the coupling assembly 5 being connected thereto. As shown in FIG. 19, the head 3 enters the receiving part 6 through the lower opening 64 and enters the hollow interior chamber 71 of the pressure element 7 through the open second end 7*b* of the pressure element 7. When the head touches the slit ring 77 of the pressure element 7, the pressure element 7 can not move upward towards the first end 6*a* of the receiving part 6 because the upper surface of the spring portions 79*a*, 79*b* abuts against the upper edge 67 of the conical recess 65 that forms the second stop.

As shown in FIG. 20, further insertion of the head 3 into the hollow interior chamber 71 expands the slit ring 77 within the widened portion 61*a* of the bore 61 of the receiving part 6. During insertion of the head 3 into the hollow interior chamber 71, the slit ring 77 expands within the widened portion 61*a* of the bore 61 of the receiving part 6. The head 3 can then be completely inserted. Because the slit ring 77 does note expand at the connection strip 75 the insertion of the head 3 may not be precisely coaxial with the central axis C but instead may be slightly out of or misaligned with the central axis C. By the further insertion of the head 3, the slit ring 77 may be expanded to a maximum extent and allows the head 3 to enter the upper portion of the hollow interior chamber 71 until it rests in the spherical segment-shaped portion of the chamber 71 that is adjacent to the second end 7*b*. Here, the slit ring 77 can elastically contract around the head 3 as shown in FIG. 20.

Figure 21A:
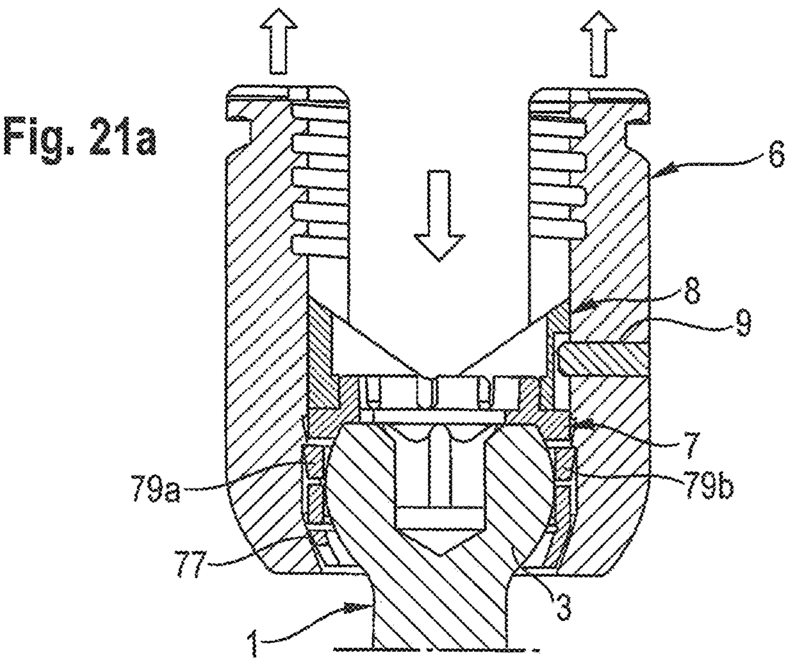
FIG. 21*a* shows a cross-sectional view of a third step of assembling the polyaxial bone anchoring device according to the first embodiment.
Figure 21B:
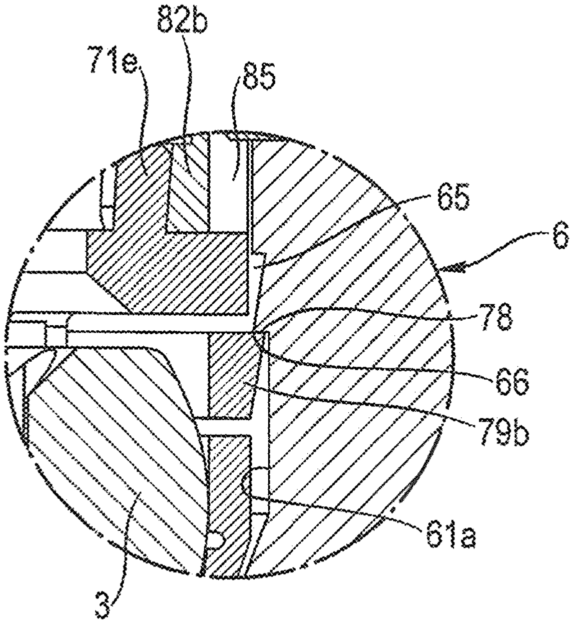
FIG. 21*b* shows an enlarged view of a detail of FIG. 21*a;*

Referring to FIGS. 21*a* and 21*b*, pulling the receiving part 6 and pressing down the pressure element 7 with an instrument (not shown) presses the slit ring 77 into the narrowing portion 61*b* of the receiving part 6. The conical shape of the recess 65 at the inner wall of the receiving part 6 provides an inclined surface that allows the spring portions 79*a*, 79*b* to slide along when the pressure element 7 is further moved downwards, thereby gradually compressing the spring portions 79*a*, 79*b* again until the upper outer edge 78 of the spring portions 79*a*, 79*b* snaps behind the second inner protrusions 66 in the receiving part 6. In this position, the pressure element is prevented from moving upwards towards the first end 6*a* of the receiving part by the first stop provided by the inner protruding edge 66. The head 3 is already clamped by the slit ring 77. Because the slit ring 77 is located between the head and the narrowing portion 61*b* of the receiving part 6, the lower opening 64 of the receiving part 6 is narrowed and the head 3 is prevented from falling out or being pushed out through the lower opening 64. This is the pre-locking condition.

In the clinical use, usually at least two bone anchoring devices are inserted into the bone and the receiving parts are aligned. The head 3 of the bone anchoring element 1 is held in a pressure element 7 by a frictional force. Hence, the receiving part 6 can be easily aligned manually and its angular position is maintained by the frictional force between the head 3 and the pressure element 7.

Finally, referring to FIG. 3, the rod 100 is inserted into the receiving part 6. It rests on the upper surface of the groove 81 at substantially two longitudinal contact areas P1, P2. Then, the locking element 10 is screwed between the legs 62*a*, 62*b* of the receiving part 6. Tightening of the locking element 9 advances the locking element towards the rod until it contacts the upper rod surface. The force applied by the locking element 9 is transferred from the rod 100 to the pressure element 7. Finally, the head 3 and the rod 100 are locked. The head 3 can be locked in a specific angular position with respect to the receiving part.

The bone anchoring element can be pivoted in the direction of the recessed portion 796 at the second end 7*b* of the pressure element 7 to a greater angle than in an opposite direction.

Figure 22:
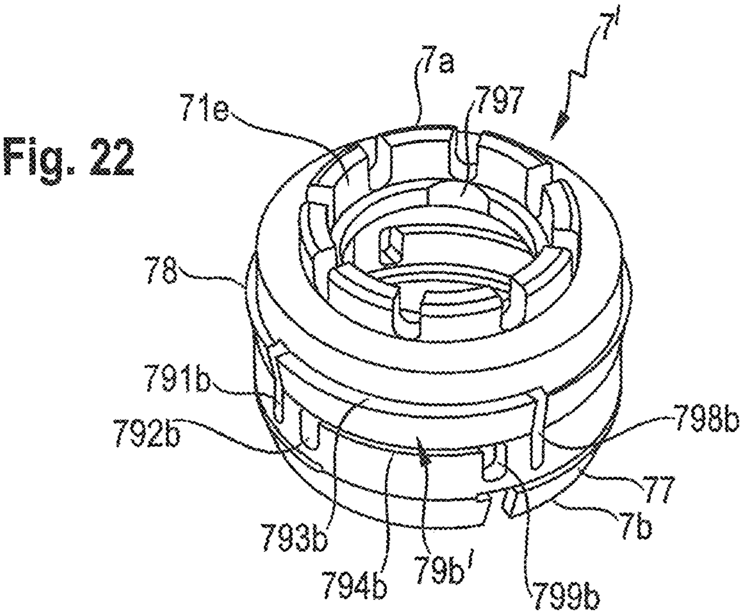
FIG. 22 shows a perspective view of a pressure element of a coupling assembly according to the second embodiment.
Figure 23:
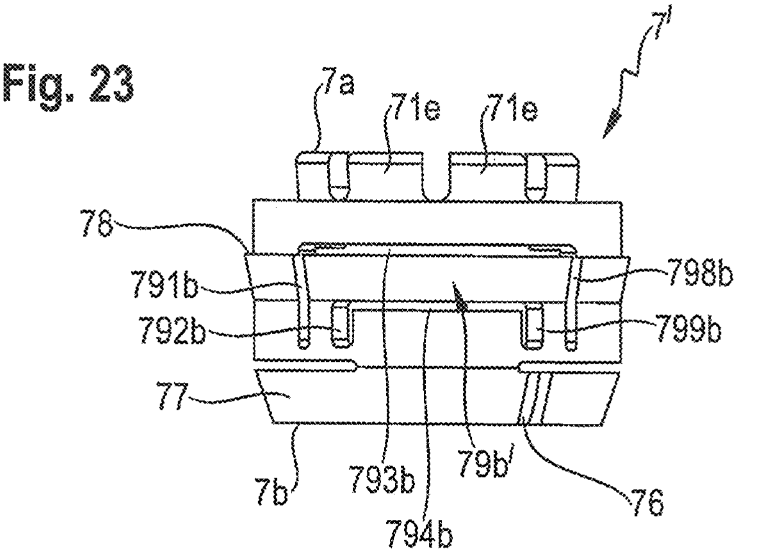
FIG. 23 shows a side view of the pressure element shown in FIG. 22.

Referring to FIGS. 22 and 23, a second embodiment of the pressure element 7 will be described. The pressure element 7' differs only in that the spring portions 79*a*', 79*b*' do not have a free end. Each spring portion 79*a*', 79*b*', respectively, is attached at the end of the ring segment-shaped portion via an axially extending strip that is generated by two vertical slits 798*a*, 798*b*, 799*a*, 799*b*, respectively, wherein one of them extends to the first horizontal slit 793*a*, 793*b* and the other extends to the second horizontal slit 794*a*, 794*b*.

A second embodiment of the rod receiving element will be described with reference to FIGS. 24 to 27. Parts and portions that are identical or similar to those of the first embodiment have the same reference numerals and the description thereof will not be repeated. The rod receiving element 8' comprises two opposite upstanding legs 86*a*, 86*b* that extend upward from the rod supporting groove 81. The upstanding legs 86*a*, 86*b* are provided by a substantially rectangular recess 86 that is cut into the hollow cylindrical rod receiving element 8' starting from the first end 8*a*. The upstanding legs 86*a*, 86*b* have such a height that they extend above the top surface of an inserted rod that rests in the rod supporting groove 81. This renders the rod receiving element 8' suitable for use with a two-part locking device 10' as depicted in FIG. 28.

The two-part locking device 10' comprises an outer locking element 10*a* and an inner locking element 10*b*. The outer locking element 10*a* cooperates with the internal thread 63 of the receiving part and is configured to abut against the first end 8*a* of the rod receiving element 8' according to the second embodiment. The inner locking element 10*b* can be screwed into a threaded hole of the outer locking element 10*a* and is configured to cooperate with the rod but not with the rod receiving element 8'. When the two-part locking element 10' is used, the head 3 of the bone anchoring element 1 can be locked by exerting pressure with the outer locking element 10*a* only onto the rod receiving element 8' according to the second embodiment and via the pressure element 7, 7' onto the head 3 and the rod can be locked independently by exerting pressure with the inner locking element 10*b* onto its surface, independently from the locking of the head 3.

Figure 28:
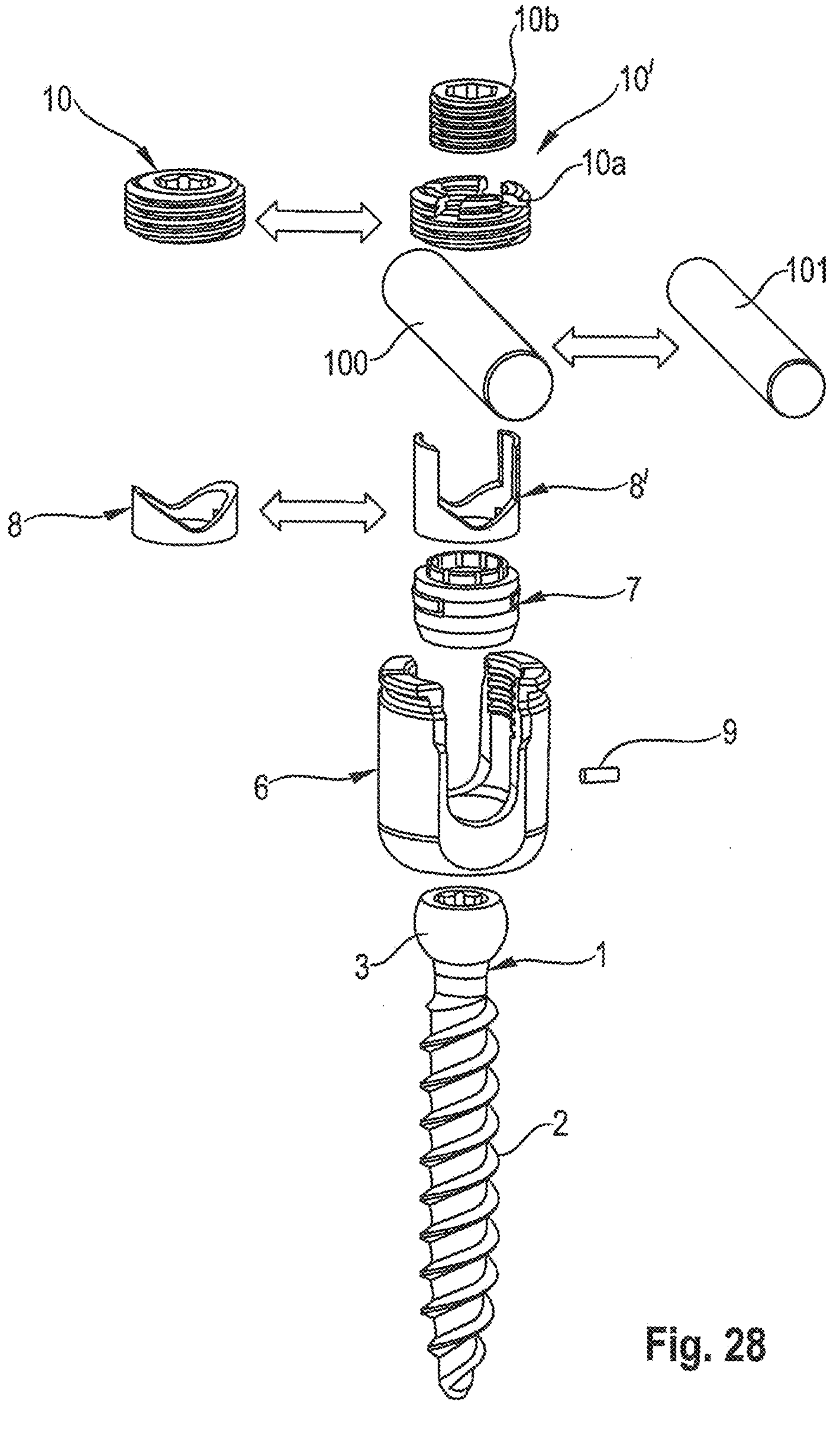
FIG. 28 shows a perspective schematic view of a modular polyaxial bone anchoring device and a modular stabilization device.

FIG. 28 depicts a modular device for stabilizing bones or vertebrae comprising a modular polyaxial bone anchoring device and different kinds of stabilization rods 100, 100' that have a different rod diameter. The modular polyaxial bone anchoring device comprises the receiving part 6 and an assembly kit comprising the coupling assembly 5 with the rod receiving element 8 according to the first embodiment and the rod receiving element 8' according to the second embodiment that can be used interchangeably together with the pressure element 7, 7'. Corresponding to a first type of coupling assembly comprising the rod receiving element 8, a single part locking device 10 is part of the modular device and corresponding to a second type of coupling assembly comprising the rod receiving element 8, the two-part locking device 10' is part of the modular device. It shall be mentioned that other types of locking devices that are configured to cooperate with either the rod receiving element 8 or the rod receiving element 8' may also be employed.

A modular polyaxial bone anchoring device further includes at least one bone anchoring element 1, preferably a plurality of bone anchoring elements that may differ in regard to their length of the shank, anchoring features of the shank, such as different thread types, thread pitches, different diameter of the shank, cannulated or non-cannulated shanks or regarding other features. Because the polyaxial bone anchoring device is a bottom loading type polyaxial bone anchoring device, the assembly of the polyaxial bone anchoring device is easily made, for example, by the surgeon or any personnel assisting the surgeon so that a suitable bone anchoring device can be provided on demand during or before surgery.

The modular stabilization device further includes at least two rods 100, 101 having a different diameter and/or at least one rod having sections with different diameter.

FIGS. 29*a* to 30*b* show various combinations of the elements of the modular system depicted in FIG. 28. In FIG. 29*a* the first type of coupling assembly using the first type of rod receiving element 8 is used together with a rod 100 of a larger diameter and a single part locking device 10. The locking device 10 exerts pressure onto the rod and locks the rod and the head 3 simultaneously. In FIG. 29*b* the first type of coupling assembly as shown in FIG. 29*a* is used together with a rod 101 having a smaller diameter than the rod 100 shown in FIG. 29*a*. The single part locking device 10 exerts pressure onto the rod with a smaller diameter and simultaneously locks the head and the rod. The rod with the smaller diameter is safely clamped in the same manner as the rod with the larger diameter.

In FIG. 30*a* the second type of coupling assembly using the second type or rod receiving element 8' is used together with the rod 100 having a larger diameter and with a two-part locking device 10'. The outer locking element 10*a* acts onto the first end 8*a* of the rod receiving element 8' which in turn transfers the force onto the pressure element 7 and locks the head 3. The rod can still be moved in axial direction and can be locked independently by the inner locking element 10*b* that exerts pressure onto the rod but not onto the head. FIG. 30*b* shows the same situation as in FIG. 30*a* with the only difference that the rod 101 having a smaller diameter than the rod shown in FIG. 30*a* is used. The inner locking element 10*b* has to be screwed deeper into the outer locking element in order to clamp the rod.

Various modifications of the embodiments described before may be contemplated. The receiving part is not limited to the exact shape as shown. The recess 62 of the receiving part does not have to have an exact U-shape. The bore 61 can have several sections with different width, as long as the enlarged portion 61*a* that provides base for the expansion of the pressure element is provided. The narrowing portion at the bottom of the receiving part is shown to be tapered, but can also be rounded. Also, the external surface of the lower portion at the bottom end of the pressure element 7, 7' can be rounded. Combinations of the surfaces of the receiving part and the pressure element that cooperate to clamp the head can be tapered and tapered, tapered and rounded and vice versa or rounded and rounded.

The embodiment has been described with one single ring segment-shaped section that clamps the head. However, there may be more than one ring segment-shaped sections to clamp the head.

The horizontal and vertical slits need not to be exactly horizontal or exactly vertical, they may have an inclinations or a shape that differs from a straight or a circular shape in order to achieve different elastic properties.

The interior hollow chamber of the pressure element and the head of the bone anchoring element can have a shape that restricts the pivoting of the bone anchoring element to one single plane so that the pivot connection is not polyaxial but monoplanar.

It is also possible to provide more than one, for example two or three recessed portions at the second end of the pressure element for having more than one directions with an enlarged pivot angle. The recessed portion at the second end of the pressure element can also be omitted so that the pivot angle is the same in all directions.

All kinds of rods can be used. While rods with a smooth surface are shown, roughened rods or rods having a structure may be used. The rods may also be rods made of a flexible material or having flexibility through other means.

While a number of different embodiments are disclosed herein, it is appreciated that different components from the different embodiments can be mixed and matched to produce a variety of still other different embodiments.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A bone anchoring device for coupling a rod to bone, the bone anchoring device comprising:

a bone anchoring element comprising a shank for anchoring to bone and a head;

a receiving part having a first end, a second end below the first end, a central axis extending through the first and second ends, a channel at the first end for receiving the rod, and an accommodation space for accommodating the head of the bone anchoring element, the accommodation space defining an opening at the second end;

a rod receiving element movable in the receiving part, wherein at least part of the rod receiving element is positionable axially lower in the receiving part than a bottom of the channel for the rod, wherein the rod receiving element comprises a rod contacting surface that forms a transverse recess for receiving the rod, and wherein the recess has an axial depth that is less than half of a greatest width of the recess; and a separate seat movable in the accommodation space, wherein the seat comprises an upwardly facing surface configured to directly engage and exert an upward pressure directed towards the first end of the receiving part on the head;

wherein the seat is configured to assume an insertion position in the receiving part where the head of the bone anchoring element is insertable through the opening of the receiving part into the seat; and wherein the rod receiving element is movable downwardly to adjust the seat from the insertion position to a pre-locking position where the head is restricted from being removed through the opening of the receiving part, while an abutment that is positioned axially lower in the receiving part than a lowermost end surface of the entire rod receiving element restricts movement of the seat from the pre-locking position back towards the insertion position.

2. The bone anchoring device of claim 1, wherein the seat is formed as part of a pressure element, and wherein the pressure element is further configured to exert a downward pressure directed towards the second end of the receiving part on the head.

3. The bone anchoring device of claim 1, wherein the seat is radially expandable to facilitate passing of the head therethrough.

4. The bone anchoring device of claim 3, the seat is expandable at the insertion position, and is restricted from expanding at the pre-locking position.

5. The bone anchoring device of claim 3, wherein the seat is ring segment-shaped.

6. The bone anchoring device of claim 1, wherein the rod receiving element and the seat are directly engageable with one another in the receiving part.

7. The bone anchoring device of claim 1, wherein the abutment is formed on the receiving part.

8. The bone anchoring device of claim 1, wherein the abutment directly engages the seat to restrict movement of the seat back towards the insertion position.

9. The bone anchoring device of claim 1, wherein the rod receiving element is configured to directly engage the seat when the rod receiving element is moved downwardly to adjust the seat from the insertion position to the pre-locking position.

10. The bone anchoring device of claim 1, wherein the rod receiving element and the seat are movable axially relative to one another in the receiving part.

11. The bone anchoring device of claim 1, wherein the recess of the rod receiving element is V-shaped.

12. A bone anchoring device for coupling a rod to bone, the bone anchoring device comprising:

a bone anchoring element comprising a shank for anchoring to bone and a head;

a receiving part having a first end, a second end below the first end, a central axis extending through the first and second ends, a channel at the first end for receiving the rod, and an accommodation space at the second end for accommodating the head of the bone anchoring element;

a first spring separable from and positionable in the receiving part and configured to extend continuously more than halfway around the central axis in a circumferential direction; and a second spring separable from and positionable in the receiving part, wherein the second spring is sized or shaped differently from the first spring;

wherein when the first and second springs are in the receiving part, at least part of each of the first and second springs is positionable axially lower in the receiving part than a bottom of the channel for the rod, and both the first and second springs are expandable in a radial direction relative to the central axis, with the first and second springs being expandable completely independently from one another; and wherein when the head is in the accommodation space, the first and second springs are pivotable together with the receiving part relative to the head.

13. The bone anchoring device of claim 12, wherein the head is insertable from the second end of the receiving part into the accommodation space.

14. The bone anchoring device of claim 12, wherein the first spring forms a seat that is configured to hold the head in the receiving part.

15. The bone anchoring device of claim 14, wherein when the head is held in the receiving part by the first spring, the second spring is configured to restrict expansion of the first spring to restrict removal of the head from the receiving part.

16. The bone anchoring device of claim 12, wherein the first and second springs are formed as respective parts of a monolithic pressure element.

17. The bone anchoring device of claim 12, wherein the first spring is ring segment-shaped.

18. The bone anchoring device of claim 12, wherein the second spring is ring segment-shaped.

19. The bone anchoring device of claim 12, wherein the first and second springs are configured to be spaced apart axially from one another in the receiving part.

20. The bone anchoring device of claim 12, wherein the first and second springs are movable at least partially axially relative to one another.

21. A bone anchoring device for coupling a rod to bone, the bone anchoring device comprising:

a bone anchoring element comprising a shank for anchoring to bone and a head;

a receiving part having a first end, a second end below the first end, a central axis extending through the first and second ends, a channel at the first end for receiving the rod, and an accommodation space for accommodating the head of the bone anchoring element, the accommodation space defining an opening at the second end; and a seat positionable in the accommodation space for holding the head in the receiving part, wherein the seat defines a slit that extends completely through the seat to render the seat radially expandable, and a recessed portion that is spaced apart from the slit in a circumferential direction with at least part of the recessed portion being at a same axial position on the seat as at least part of the slit, and wherein for at least one cross-sectional plane that extends perpendicularly to the central axis and that extends through the slit, a resulting cross-section of the seat is configured to extend continuously more than halfway around the central axis in the circumferential direction;

wherein the seat is configured to assume an insertion position in the receiving part where the head of the bone anchoring element is insertable through the opening of the receiving part into the seat; and wherein when the head and the seat are in the receiving part with the recessed portion of the seat oriented at a first radial direction relative to the central axis, the recessed portion facilitates pivoting of the bone anchoring element to a greater angle relative to the receiving part in the first radial direction than in another radial direction different from the first radial direction.

22. The bone anchoring device of claim 21, wherein the seat is rotatable relative to the receiving part such that the orientation of the first radial direction is adjustable around the central axis.

23. The bone anchoring device of claim 21, wherein the seat has opposing upwardly and downwardly facing end faces, and wherein the slit extends continuously from the upwardly facing end face to the downwardly facing end face to render the seat radially expandable.

24. The bone anchoring device of claim 21, wherein the seat is formed as part of a pressure element, and wherein the pressure element is further configured to exert a downward pressure directed towards the second end of the receiving part on the head.

* * * * *